United States Patent
Frey, II et al.

(10) Patent No.: US 8,622,993 B2
(45) Date of Patent: Jan. 7, 2014

(54) DEVICE AND METHOD FOR DELIVERING THERAPEUTIC SUBSTANCES TO THE MAXILLARY SINUS OF A PATIENT

(75) Inventors: William H. Frey, II, White Bear Lake, MN (US); Neil J. Johnson, Edina, MN (US)

(73) Assignee: HealthPartners Research Foundation, Minneapolis, MN (US)

( * ) Notice: Subject to any disclaimer, the term of this patent is extended or adjusted under 35 U.S.C. 154(b) by 116 days.

(21) Appl. No.: 12/967,300

(22) Filed: Dec. 14, 2010

(65) Prior Publication Data

US 2011/0151393 A1    Jun. 23, 2011

Related U.S. Application Data

(60) Provisional application No. 61/287,937, filed on Dec. 18, 2009.

(51) Int. Cl.
*A61M 31/00* (2006.01)

(52) U.S. Cl.
USPC .......................................... 604/514; 433/229

(58) Field of Classification Search
USPC ........... 604/73, 132, 217, 257–262, 500, 514, 604/516; 433/24, 215, 224, 229
See application file for complete search history.

(56) References Cited

U.S. PATENT DOCUMENTS

| | | |
|---|---|---|
| 6,413,499 B1 | 7/2002 | Clay |
| 2003/0133877 A1 | 7/2003 | Levin |
| 2005/0031651 A1 | 2/2005 | Gervais et al. |
| 2007/0004743 A1 | 1/2007 | Xiao et al. |
| 2007/0017508 A1* | 1/2007 | Rasor et al. .............. 128/200.24 |
| 2007/0093420 A1 | 4/2007 | Yeomans et al. |
| 2008/0038703 A1* | 2/2008 | Segal et al. .................. 434/264 |
| 2009/0306624 A1 | 12/2009 | Arensdorf et al. |
| 2010/0016267 A1 | 1/2010 | Theeuwes et al. |
| 2010/0076269 A1 | 3/2010 | Makower et al. |

OTHER PUBLICATIONS

Wagner et al. "A Phase II, Double-Blind, Randomized, Placebo-Controlled Clinical Trial of tgAAVCF Using Maxillary Sinus Delivery in Patients with Cystic Fibrosis with Antrostomies". Human Gene Therapy. Jul. 2002, 13(11): 1349-1359.*
John A. Wagner et al., "A Phase II, Double-Blind, Randomized, Placebo-Controlled Clinical Trial of tgAAVCF Using Maxillary Sinus Delivery in Patients with Cystic Fibrosis with Antrostomies", Human Gene Therapy 13:1349-1359 (Jul. 20, 2002).
International Search Report from related PCT application No. PCT/US10/60665.

* cited by examiner

*Primary Examiner* — Kami A Bosworth
(74) *Attorney, Agent, or Firm* — Winthrop & Weinstine, P.A.

(57) ABSTRACT

The present invention is directed to devices and methods for administering at least one effective dose of at least one therapeutic substance to at least one of the maxillary sinuses of a patient in need thereof. Alternate embodiments may comprise administration of the at least one effective dose of at least one therapeutic substance to both maxillary sinuses, where the administered therapeutic substance(s) are either the same or differ from sinus to sinus. Still further alternative embodiments may comprise more than an initial effective dose administered to a patient's maxillary sinus(es), so that the therapeutic substance may be delivered over time, thereby requiring a larger dose be deposited within at least one of the maxillary sinuses so that the maxillary sinus(es) serve as a therapeutic substance depot for long-term release to the target structure(s).

9 Claims, 1 Drawing Sheet

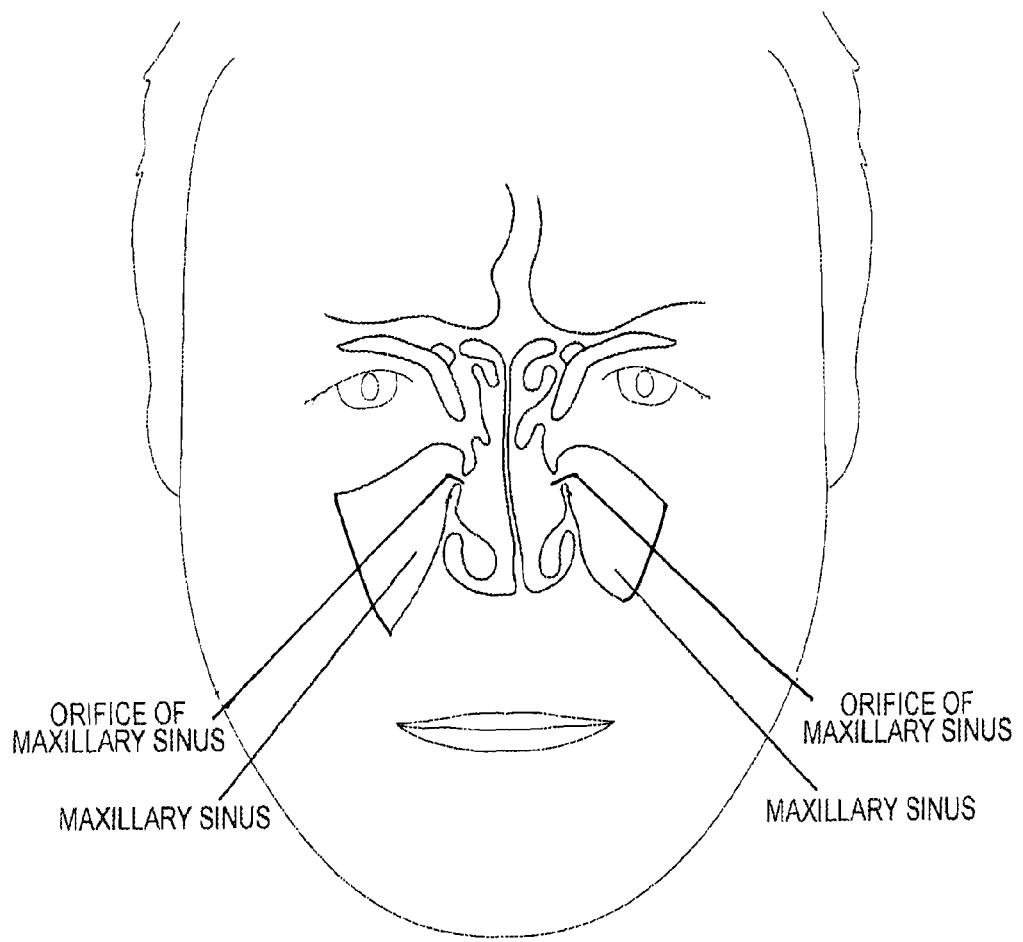

DEVICE AND METHOD FOR DELIVERING THERAPEUTIC SUBSTANCES TO THE MAXILLARY SINUS OF A PATIENT

CROSS-REFERENCE TO RELATED APPLICATIONS

This application claims the benefit and priority of U.S. provisional patent application Ser. No. 61/287,937 filed Dec. 18, 2009, the entire contents of which are expressly incorporated by reference herein.

BACKGROUND OF THE INVENTION

1. Field of the Invention

The present invention is directed to devices and methods for administering at least one effective dose of at least one therapeutic substance to at least one of the maxillary sinuses of a patient in need thereof. Alternate embodiments may comprise administration of the at least one effective dose of at least one therapeutic substance to both maxillary sinuses, where the administered therapeutic substance(s) are either the same or differ from sinus to sinus. Still further alternative embodiments may comprise more than an initial effective dose administered to a patient's maxillary sinus(es), so that the therapeutic substance may be delivered over time, thereby requiring a larger dose be deposited within at least one of the maxillary sinuses so that the maxillary sinus(es) serve as a therapeutic substance depot for long-term release to the target structure(s).

2. Description of the Related Art

It is known that intranasal delivery of therapeutic substances to patients pre or post-stroke, or those diagnosed with disorders involving neurological impairments, e.g., Alzheimer's disease, Parkinson's disease, stroke, traumatic brain injury, spinal cord injury can be an effective treatment for the condition. See, e.g., Reger M A, Watson G S, Green P S, Wilkinson C W, Baker L D, Cholerton B, Fishel M A, Plymate S R, Breitner J C, DeGroodt W, Mehta P, Craft S. Intranasal insulin improves cognition and modulates beta-amyloid in early AD. Neurology 70:440-448 (2008).

Intranasal delivery to the upper one-third of the patient's nasal cavity provides a non-invasive method of bypassing the blood-brain barrier (BBB) in order to rapidly deliver therapeutic substances directly to the target organ and/or region. For example, and without limitation, such targeted intranasal administration to the upper one-third of the nasal cavity of a therapeutic substance delivers the substance directly to the brain, spinal cord, lymphatics and the vessel walls of cerebrovasculature for treating and/or preventing central nervous system (CNS) disorders such as Alzheimer's disease, Parkinson's disease, stroke, traumatic brain injury, brain tumors. This known method allows drugs, therapeutic proteins, polynucleotides, viral vectors and the like, i.e., compounds that do not normally cross the BBB, to be delivered directly to the CNS with minimal systemic exposure.

Thus, intranasal delivery allows specific targeting of therapeutic substance to the CNS. In particular, targeting the upper one-third of the nasal cavity with the therapeutic substance is most effective and efficient in delivering the administered dose to the patient's CNS. This delivery technique, inter alia, is desirable because it avoids a first-pass elimination by the liver and/or kidneys, thereby allowing a lower therapeutic dose to be used, and minimizing systemic exposure to non-target organs, etc., resulting in fewer undesirable or even dangerous side effects.

More general intranasal delivery, generally defined herein as administration of a therapeutic substance to the upper one-third and/or lower two-thirds of a patient's nasal cavity is known to utilize both the olfactory and trigeminal nerves as a conduit to the CNS. Delivery of the therapeutic substance along the olfactory and trigeminal pathways allows the effective bypassing of the BBB. However, the more general intranasal administration or delivery results in some undesirable and potentially dangerous systemic exposure.

It is also known that greater than 98% of small molecule and nearly 100% of large molecule CNS drugs developed by the pharmaceutical industry do not cross the BBB. Intracerebroventricular or intraparenchymal drug administration can directly deliver therapeutics to the brain; however, these methods are invasive, inconvenient, and impractical for the numbers of individuals requiring therapeutic interventions for treating CNS disorders. Intranasal drug administration is a non-invasive and convenient means to rapidly target therapeutics of varying physical and chemical properties to the CNS. The olfactory and trigeminal neural pathways connecting the nasal passages to the CNS are clearly involved in the delivery of therapeutic compounds applied via intranasal administration to the upper third of the nasal cavity. In addition to these neural pathways, perivascular pathways, and pathways involving the cerebrospinal fluid or nasal lymphatics may play a central role in the distribution of therapeutics from the nasal cavity to the CNS. See, e.g., Dhuria, S V, Hanson, L R and Frey, W H II (2010) Journal of Pharmaceutical Sciences 99(4):1654-1673, *Intranasal delivery to the central nervous system: mechanisms and experimental considerations*. Numerous therapeutics have been delivered to the CNS following intranasal administration, to both the upper third and lower two-thirds of the nasal cavity, and have demonstrated pharmacological effects in animals and in humans.

The intranasal method of drug delivery holds great promise as an alternative to more invasive routes, particularly administration to the upper one-third of the nasal cavity, however, a number of factors limit the efficiency of intranasal delivery to the CNS. Absorption of intranasally applied drugs into the capillary network in the nasal mucosa can decrease the amount of drug available for direct transport into the CNS. Additional factors within the nasal cavity, including the presence of nasal mucociliary clearance mechanisms, metabolizing enzymes, efflux transporters and nasal congestion can also reduce the efficiency of delivery into the CNS. In particular, therapeutic compounds may be absorbed into the blood and/or delivered to peripheral (non-target) tissues, thus reducing delivery of the compound to the target. As a result, the efficacy of administering therapeutic compounds to the lower two-thirds of the nasal cavity with the goal of delivering therapeutics to the CNS is greatly diminished. Further, the efficacy of administering therapeutic compounds to the upper one-third of the nasal cavity as a means to target therapeutics to the CNS could be improved. For example, current methods require a single effective dose be delivered when needed to the upper one-third of the nasal cavity, repeated as necessary per the treatment plan. This requires patient compliance with a repeated application, which is generally less than optimal. In addition, intranasal administration may be somewhat uncomfortable, further diminishing patient compliance. Moreover, general intranasal administration, or even administration to the upper one-third of the patient's nasal cavity, involves the olfactory nerves which innervate some different structures than does the trigeminal nerve. Therefore, intranasal administration cannot target only those structures innervated by the trigeminal nerve.

It is desirable then to provide devices and methods for administering at least one effective dose of at least one therapeutic substance to target at least one structure that is innervated by the trigeminal nerve and/or is in operative or fluid communication with the maxillary sinus. Since the trigeminal nerve passes through the maxillary sinus, the sinus cavity may be used as a repository for at least one therapeutic substance. Alternate embodiments may comprise administration of the at least one effective dose of at least one therapeutic substance to both maxillary sinuses, where the administered therapeutic substance(s) are either the same or differ from sinus to sinus. Still further alternative embodiments may comprise more than an initial effective dose administered to a patient's maxillary sinus(es), so that the therapeutic substance may be delivered over time, thereby requiring a larger dose be deposited within at least one of the maxillary sinuses so that the maxillary sinus(es) serve as a therapeutic substance depot for long-term release to the target structure(s).

Current devices and methods access one or more maxillary sinuses with a catheter for a lavage, e.g., to flush infected sinus areas. These devices only serve to clean out the nasal cavity where the catheter is placed, and only partially reach the sinus with a large volume of fluid flushing the nasal cavity. Thus, these devices are poorly targeted and not designed for purposes of delivering a therapeutic substance to the maxillary sinus cavity. There are also known implantable devices requiring surgery which leads to inflammation in the area and has the potential to lead to infection. Further, none of these methods comprise an effective dose of a therapeutic substance to treat a structure either remote from and in operative communication with the maxillary sinus, e.g., the patient's CNS, or innervated by the trigeminal nerve and thereby in operative communication with the maxillary sinus.

Further, current devices and methods may, via general inhalation methods, enable a very small, i.e., much less than 0.1 milliliter, of the inhaled substance to make its way through the tortuous pathway from the nostril and into the maxillary sinus. To make this journey via inhalation, the therapeutic substance must travel between the lower and middle concha, pass over and into the semilunar hiatus, travel superiorly into the maxillary sinus opening, resist the ciliated action of the ostium/tube passing into the maxillary sinus and ultimately moving into the sinus itself. The vast remainder of the inhaled substance is given to the general system, resulting in unnecessary exposure, poor targeting of subject organs/structures. Thus, a large overdosing of the substance is required in order to provide a therapeutic amount to the subject organ/structure, the remaining dose being delivered to the system with resulting undesirable and often dangerous side effects. The methods and devices of the present invention enable a full effective dose(s) to be deposited directly into the maxillary sinus without any systemic exposure.

BRIEF SUMMARY OF THE INVENTION

Given the situation described above there is a need for devices and methods for administering at least one effective dose of at least one therapeutic substance to at least one of the maxillary sinuses of a patient in need thereof for subsequent transport along the trigeminal nerve pathway to target the CNS, oral structures and/or facial structures. Alternate embodiments may comprise administration of the at least one effective dose of at least one therapeutic substance to both maxillary sinuses, where the administered therapeutic substance(s) are either the same or differ from sinus to sinus. Still further alternative embodiments may comprise more than an initial effective dose administered to a patient's maxillary sinus(es), so that the therapeutic substance may be delivered over time, thereby requiring a larger dose be deposited within at least one of the maxillary sinuses so that the maxillary sinus(es) serve as a therapeutic substance depot for long-term release to the target structure(s).

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

FIG. 1 is an anatomical cutaway illustrating the nasal cavity, orifice of maxillary sinus and maxillary sinus on either side of the patient's face.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

DEFINITIONS

As used herein, "central nervous system" (CNS) refers to the brain and spinal cord and associated tissues.

As used herein, "neurological disorder" comprises conditions involving ischemia, i.e., cerebral ischemia, ischemia, stroke, neurodegeneration, neurological complications arising from coronary bypass surgery, Parkinson's disease, Wilson's disease, Huntington's disease, amyotrophic lateral sclerosis, Alzheimer's disease, iron and copper toxicity, iron overload in the brain, thalassemia, metal poisoning of the central nervous system, central nervous system oxidative stress, traumatic brain injury, and spinal cord injury. Further, dental pain, TMJ, headache, trigeminal neuralgia may also be considered neurological disorders for the present invention. In addition, virtually any neurological or psychiatric disorder may be treated by targeting the appropriate drug/therapeutic substance to the trigeminal pathway by way of the maxillary sinus under the present invention. Each such disorder is within the scope of the present invention.

An "effective amount" or "dose" of agent is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and overcome the disease itself.

In the context of the present invention, the terms "treat" and "therapy" and "therapeutic" and the like refer to alleviate, slow the progression, prophylaxis, attenuation or cure of ischemia, trauma, metal poisoning or neurodegeneration. Further, dental pain, TMJ, headache, trigeminal neuralgia may also be considered neurological disorders for the present invention. In addition, virtually any neurological or psychiatric disorder may be treated by targeting the appropriate drug/therapeutic substance to the trigeminal pathway by way of the maxillary sinus under the present invention. Each such disorder is within the scope of the present invention.

"Prevent", as used herein, refers to putting off, delaying, slowing, inhibiting, or otherwise stopping, reducing or ameliorating the onset of ischemia, trauma, metal poisoning or neurodegeneration. Further, dental pain, TMJ, headache, trigeminal neuralgia may also be considered neurological disorders for the present invention. In addition, virtually any neurological or psychiatric disorder may be treated by targeting the appropriate drug/therapeutic substance to the trigeminal pathway by way of the maxillary sinus under the present invention. Each such disorder is within the scope of the present invention.

It is preferred that a large enough quantity of the agent be applied in non-toxic levels in order to provide an effective level of neuroprotection. The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

Ischemia or ischemic episode or condition is defined herein to comprise an ischemic condition where the brain or parts of the brain do not receive enough blood flow to maintain normal neurologic function. Various conditions can cause ischemia, including but not limited to stroke.

Applicants hereby incorporate by reference in its entirety, the following publication, co-authored by the co-inventors of the present invention: Johnson et al., Trigeminal Pathways Delivery a Low Molecular weight Drug from the Nose to the Brain and Orofacial Structures, Molecular Pharmaceutics Vol. 7, No. 3, 884-893 (2010). In this publication, the authors provide evidence that, inter alia, the trigeminal nerve which passes through the maxillary sinus, is a bi-directional conduit which may serve to transport a therapeutic substance to the CNS as well as oral and facial structures.

In a published patent application, U.S. Pat. No. 7,084,126 by William H. Frey II (also a co-inventor of the present application), et al., entitled METHODS AND COMPOSITIONS FOR ENHANCING CELLULAR FUNCTION THROUGH PROTECTION OF TISSUE COMPONENTS, a variety of agents are disclosed for protecting muscarinic receptors in subjects in need thereof, wherein the agent may be administered directly to the brain, bypassing the BBB, by delivery of the agent to the upper one-third of the patient's nasal cavity. Similarly, certain diseases and conditions are disclosed which may be treated, including protection by pretreating the subject at risk of developing certain diseases and/or conditions, by administration of the disclosed agents, including but not limited to, pyrophosphate analogs, imidodiphosphates, polyphosphates, bisphosphonates, bilirubin, biliverdin, carnosol, quercetin, myricetin, and catalase, peroxidase. The entire contents of this document are hereby incorporated by reference.

Also, the entire contents of the following divisional patent applications from U.S. Pat. No. 7,084,126 to Frey et al., are expressly incorporated by reference herein:

US Patent Application printed publication number 20060009413 to Frey II et al., entitled METHODS AND COMPOSITIONS FOR PROTECTING OR TREATING MUSCARINIC RECEPTORS THROUGH ADMINISTRATION OF PYROPHOSPHATE ANALOGS IN SUBJECTS EXPOSED TO TOXIC OR CARCINOGENIC METALS OR METAL IONS;

US Patent Application printed publication number 20060014716 to Frey et al., entitled METHODS AND COMPOSITIONS FOR PROTECTING AND TREATING MUSCARINIC RECEPTORS BY ADMINISTERING A PYROPHOSPHATE ANALOG TO A SUBJECT EXPOSED TO BACTERIAL, FUNGAL, VIRAL, PRION OR ALGAL INFECTION;

US Patent Application printed publication number 20060030542 to Frey et al., entitled METHODS AND COMPOSITIONS FOR INCREASING THE EFFICACY OF AN AGENT THAT DIRECTLY OR INDIRECTLY AFFECTS A MUSCARINIC RECEPTOR THROUGH ADMINISTRATION OF A PYROPHOSPHATE ANALOG; and US Patent Application printed publication number 20060272642 to Frey et al., entitled METHODS AND COMPOSITIONS FOR PROTECTING AND TREATING AT LEAST ONE MUSCARINIC RECEPTOR FROM DYSFUNCTION NOT RESULTING FROM OXIDATIVE STRESS, TOXIC ACTIONS OF METALS OR INFECTIOUS AGENTS BY ADMINISTERING A PYROPHOSPHATE ANALOG.

The entire contents of U.S. Pat. No. 7,786,166 to Frey et al., entitled METHODS AND COMPOSITIONS FOR PROTECTING AND TREATING MUSCARINIC RECEPTORS THROUGH ADMINISTRATION OF AT LEAST ONE PROTECTIVE AGENT is also a divisional of U.S. Pat. No. 7,084,126 to Frey et al, are also expressly incorporated by reference herein.

The entire contents of U.S. Pat. No. 7,618,615 to Frey et al., entitled METHODS FOR PROVIDING NEUROPROTECTION FOR THE ANIMAL CENTRAL NERVOUS SYSTEM AGAINST NEURODEGENERATION CAUSED BY ISCHEMIA, are expressly incorporated by reference herein. U.S. Pat. No. 7,618,615 discloses, inter alia, administration of at least one effective dose of deferoxamine (DFO) to the upper one-third of a patient's nasal cavity to treat a patient suffering from neurodegeneration caused by ischemia.

Also incorporated by reference in its entirety is U.S. Pat. No. 7,776,312 to Frey et al., a continuation-in-part of U.S. Pat. No. 7,618,615, entitled METHOD OF TREATING ALZHEIMER'S DISEASE COMPRISING ADMINISTERING DEFEROXAMINE (DFO) TO THE UPPER ONE-THIRD OF THE NASAL CAVITY.

Continuation application from U.S. Pat. No. 7,776,312 to Frey et al., entitled METHODS AND PHARMACEUTICAL COMPOSITIONS FOR DIFFERENTIALLY ALTERING GENE EXPRESSION TO PROVIDE NEUROPROTECTION FOR THE ANIMAL CENTRAL NERVOUS SYSTEM AGAINST THE EFFECTS OF ISCHEMIA, NEURODEGENERATION, TRAUMA AND METAL POISONING, is also expressly incorporated in its entirety herein by reference.

Finally, US Patent Application printed publication number 20100061959, entitled METHODS FOR PROVIDING NEUROPROTECTION FOR THE ANIMAL CENTRAL NERVOUS SYSTEM AGAINST THE EFFECTS OF ISCHEMIA, NEURODEGENERATION, TRAUMA AND METAL POISONING, A CONTINUATION OF U.S. Pat. No. 7,618,615 to Frey et al., is expressly incorporated in its entirety herein by reference.

The US patent and applications incorporated herein by reference supra are included to provide a fully developed experimental and developmental basis for the present invention's use of various compounds to treat various diseases and/or conditions using the maxillary sinus as a therapeutic substance depository followed by use of the trigeminal nerve as a bi-directional transport conduit. Each of the incorporated references comprises intranasal administration to the upper one-third of the nasal cavity. Therefore, the trigeminal nerve pathway is engaged by the methods of the incorporated references, but at a completely different anatomical location than the present invention. In addition, as discussed above and unlike the present invention, the intranasal methods engage the olfactory nerves in addition to the trigeminal nerves. Further, the present invention comprises a therapeutic substance deposition site which is far more amenable to precise administration of at least one effective dose, with subsequent delivery to targeted structures, without any systemic exposure.

Notwithstanding these differences, Applicants have discovered that the compounds/therapeutic substances and/or agents, the diseases and/or conditions, and the data obtained for structures that are innervated by the trigeminal nerve disclosed in the incorporated references are valid for non-obvious and novel use and application in the present invention. Thus, the doses, e.g., used for intranasal administration of DFO to the upper third of the patient's nasal cavity provided in some of the incorporated references may be applied very directly to the present invention. The present invention utilizes, inter alia, the maxillary sinus(es) as a depository or repository for a single effective dose of a therapeutic substance(s) in certain embodiments, or more than a single effective dose in other embodiments, i.e., at least one effective dose, and then utilizes the fact that the trigeminal nerve passes through the maxillary sinus drug repository in order to target the deposited therapeutic substance to a certain structure and/or region that is innervated by the trigeminal nerve and/or in operative or fluid communication with the maxillary sinus, e.g., the CNS, oral/facial structures, nasal associated lymphatics and the like. The Experimental data presented herein demonstrates that therapeutic substances deposited in the maxillary sinus are transported and delivered to these structures.

The maxillary sinus is in fluid communication with the patient's nasal cavity and comprises right and left maxillary sinuses. Each maxillary sinus communicates with the corresponding nasal passage via the orifice of the maxillary sinus. The maximum volume of the maxillary sinus in adults is approximately 4 to 15 ml, though individual sinuses may comprise volumes outside of this range.

The pathway from the nasal passages to the corresponding orifice of maxillary sinus, and ultimately to the corresponding maxillary sinus forms the basis for the present invention. This fluid pathway allows for a device to be inserted into the nasal passage to the orifice of the maxillary sinus, whereupon at least one effective amount or dose of at least one therapeutic substance may be administered and delivered into the maxillary sinus. As noted above, the pathway to the maxillary sinus is tortuous and requires: traversing the nostril, moving through the region between the lower and middle concha, navigating over and into the semilunar hiatus, traveling superiorly into the maxillary sinus opening, resisting the ciliated action of the ostium/tube passing into the maxillary sinus and ultimately moving into the sinus itself.

Since the trigeminal nerve passes through the maxillary sinus, the therapeutic substance(s) now residing in the maxillary sinus after delivery therein will be moved along the trigeminal nerve to structures innervated by the trigeminal nerve as demonstrated herein. For example, oral and facial structures, as well as nasal associated lymphatics and deep cervical lymph nodes, may receive at least one effective amount or dose of a therapeutic substance in this manner. This targeting of the lymphatics using the present invention is also indicated for use in treating and/or preventing certain immune disorders such as Sjogren's disease, or dry eye syndrome, with symptoms of dry eyes and dry mouth. Further, the patient's central nervous system is fluidly or operatively connected with the maxillary sinus and trigeminal nerve, which allows administration and delivery of at least one therapeutic substance to the patient's CNS using the maxillary sinus as a deposition location for the therapeutic substance(s).

Exemplary Experiment 1

Table 1 illustrates data obtained from an experiment comparing the concentration of an exemplary compound, lidocaine, in selected tissue, structures and/or regions when administered by intravenous administration and intranasal administration.

Experimental Design for Exemplary Experiment 1

Rats were administered the same lidocaine dose intranasally or intravenously. After approximately 30 minutes, rats were perfused and a selected number of brain/CNS, orofacial and body structures were dissected to determine lidocaine concentrations. Tissues were pulverized and supernatant fractions were analyzed using an ELISA. Further experimental design may be found in the incorporated reference Johnson et al., Trigeminal Pathways Delivery a Low Molecular weight Drug from the Nose to the Brain and Orofacial Structures, Molecular Pharmaceutics Vol. 7, No. 3, 884-893 (2010).

Results for Exemplary Experiment 1

With reference to Table 1, blood levels of lidocaine were found to be significantly lower following intranasal administration as compared with intravenous administration. In addition, brain and spinal cord tissue, i.e., the olfactory bulb, cortex, diencephalon, midbrain, cerebellum, brainstem and upper SC, lower cervical SC, thoracic SC, lumbar SC and trigeminal ganglion, all had higher lidocaine concentrations following intranasal delivery as compared with intravenous delivery. Each of these structures comprises trigeminal innervation.

Further, orofacial structures having trigeminal innervations had higher lidocaine tissue concentrations than brain structures following intranasal delivery as well as higher lidocaine tissue concentrations following intranasal delivery as compared with lidocaine concentrations following intravenous delivery. This set of structures included the maxillary sinus, the maxillary incisor, the maxillary molar, the mandibular incisor, the mandibular molar and the tongue.

Finally, facial structures having trigeminal innervations had higher lidocaine tissue concentrations following intranasal delivery as compared with lidocaine tissue concentrations following intravenous delivery. This set of structures included the temporomandibular joint, the masseter muscle, the lacrimal gland, skin and aponeurosis on head, and the eye. It is important that the lacrimal gland is targeted under certain embodiments of the present invention as the invention may be used to treat dry eye syndrome (Sjogren's disease).

TABLE 1

Lidocaine Tissue Concentrations following Intranasal or Intravenous Administration

| tissue | [Lidocaine] mean ± SEM (µM) | | significance[b] | lidocaine targeting: ratio of tissue concn (µM)/blood concn at 25 min (µM), mean ± SEM | | drug targeting index: ratio |
|---|---|---|---|---|---|---|
| | IN | IV | | IN | IV | IN/IV, mean |
| blood | | | | | | |
| blood 5 min | 1.6 ± 0.7 | 540 ± 82 | *** | | | |
| blood 10 min | 21 ± 8.3 | 154 ± 31 | ** | | | |
| blood 15 min | 10 ± 4.6 | 77 ± 8.0 | *** | | | |
| blood 20 min | 10 ± 3.2 | 65 ± 13 | *** | | | |
| blood 25 min | 7.9 ± 1.8 | 21 ± 3.3 | * | | | |
| total AUC[c] (0-25 min) µM·min | 173 ± 93 | 3916 ± 634 | *** | | | |
| peripheral tissues | | | | | | |
| deep cervical lymph nodes | 30 ± 5.9 | 13 ± 1.6 | * | 3.8 ± 3.2 | 0.6 ± 0.5 | 6.2 |
| nasal epithelium | 4549 ± 756 | 12 ± 2.6 | *** | 577 ± 409 | 0.6 ± 0.8 | 1003 |
| urine | 48 ± 13 | 1142 ± 318 | ** | 6.1 ± 6.9 | 55 ± 97 | 0.1 |
| kidney | 80 ± 7.6 | 88 ± 16 | ns | 10 ± 4.1 | 4.2 ± 5.0 | 2.4 |
| liver | 44 ± 5.0 | 87 ± 11 | ** | 5.6 ± 2.7 | 4.1 ± 3.2 | 1.3 |
| brain and spinal cord tissue | | | | | | |
| olfactory bulb | 266 ± 47 | 8.4 ± 1.1 | *** | 34 ± 25 | 0.4 ± 0.3 | 84 |
| cortex | 33 ± 4.5 | 9.9 ± 1.6 | *** | 4.2 ± 2.4 | 0.5 ± 0.5 | 8.9 |
| diencephalon | 16 ± 4.8 | 2.0 ± 0.6 | ** | 2.1 ± 2.6 | 0.1 ± 0.2 | 22 |
| midbrain | 23 ± 3.2 | 7.3 ± 1.7 | *** | 2.9 ± 1.8 | 0.3 ± 0.5 | 8.4 |
| cerebellum | 35 ± 7.9 | 8.4 ± 1.8 | ** | 4.4 ± 4.3 | 0.4 ± 0.6 | 11 |
| brainstem and upper SC | 45 ± 11 | 8.9 ± 2.0 | ** | 5.8 ± 6.1 | 0.4 ± 0.6 | 14 |
| lower cervical SC | 24 ± 5.5 | 7.0 ± 0.7 | ** | 3.0 ± 3.0 | 0.3 ± 0.2 | 9.0 |
| thoracic SC | 21 ± 3.8 | 8.1 ± 1.1 | ** | 2.6 ± 2.0 | 0.4 ± 0.3 | 6.8 |
| lumbar SC | 19 ± 4.7 | 13 ± 3.5 | ns | 2.4 ± 2.5 | 0.6 ± 1.1 | 3.8 |
| trigeminal ganglion[d] | 147 ± 44 | 13 ± 1.5 | ** | 19 ± 24 | 0.6 ± 0.5 | 29 |
| oral structures with trigeminal innervations | | | | | | |
| maxillary sinus | 3508 ± 685 | 11 ± 2.4 | *** | 445 ± 371 | 0.5 ± 0.7 | 856 |
| maxillary incisor: SA nerve (V2) | 803 ± 253 | 3.0 ± 0.5 | ** | 102 ± 137 | 0.1 ± 0.2 | 701 |
| maxillary molar: SA nerve (V2) | 476 ± 116 | 3.1 ± 0.4 | *** | 60 ± 63 | 0.1 ± 0.1 | 413 |
| mandibular incisor: IA nerve (V3) | 148 ± 31 | 2.7 ± 0.6 | *** | 19 ± 17 | 0.1 ± 0.2 | 145 |
| mandibular molar: IA nerve (V3) | 199 ± 43 | 1.9 ± 0.8 | *** | 25 ± 24 | 0.1 ± 0.2 | 270 |
| tongue (V3) | 651 ± 35 | 8.1 ± 1.6 | *** | 83 ± 19 | 0.4 ± 0.5 | 213 |
| facial structures with trigeminal innervations | | | | | | |
| temporomandibular joint (V3) | 72 ± 27 | 7.1 ± 1.0 | *** | 9.1 ± 15 | 0.3 ± 0.3 | 27 |
| masseter muscle (V3) | 15 ± 2.7 | 4.8 ± 0.8 | * | 1.9 ± 1.4 | 0.2 ± 0.2 | 8.2 |
| lacrimal gland (VII) | 58 ± 14 | 43 ± 4.4 | ns | 7.4 ± 7.6 | 2.0 ± 1.4 | 3.6 |
| skin and aponeurosis on head (V1) | 3.6 ± 1.1 | 3.6 ± 0.5 | ns | 0.5 ± 0.6 | 0.2 ± 0.2 | 2.7 |
| eye (V1 and CN II) | 8.3 ± 1.5 | 6.5 ± 0.7 | ns | 1.1 ± 0.8 | 0.3 ± 0.2 | 3.4 |

[a]The table shows the mean and SEM (N = 6) of tissue concentrations following intranasal and intravenous administration of 8 mg of 10% lidocaine. The p value for each tissue is an unpaired t-test comparison between intranasal and IV delivery (<0.05 (*), <0.01 (), and <0.001 (*)).
[b]Significance = <0.05 (*). <0.01 (), <0.001 (*).
[c]Area under the curve.
[d]The trigeminal nerve was dissected at the base of the skull.

Exemplary Experiment 2

Experiment 2 evaluated the biodistribution of IRdye 800 10 minutes after intranasal delivery of IRdye 800.

Experimental Design for Exemplary Experiment 2

Prior to intranasal treatment with IRdye 800, rat tissue is nearly transparent at 800 nm. The body was visualized using a 700 nm filter and the IRdye 800 using a 800 nm filter. The two images obtained were then overlayed in order to visualize the movement and biodistribution of IRdye 800 after intranasal delivery. Infrared imaging was performed for 30 minutes prior to euthanasia and tissue collection. Following perfusion, the brain was removed, sectioned and imaged. Selected tissues were also removed and imaged. Concentrations of IRdye 800 were obtained using an Odyssey scanner and ranging from 10 nM to 100 µM. If the dye was visible to the naked eye, it was classified as >100 µM. Further experimental design details may be seen in the incorporated reference Johnson et al., Trigeminal Pathways Delivery a Low Molecular weight Drug from the Nose to the Brain and Orofacial Structures, Molecular Pharmaceutics Vol. 7, No. 3, 884-893 (2010).

Results for Exemplary Experiment 2

At 0 minutes, i.e., immediately after first drop of IRdye 800 is administered, it is seen in the nasal cavity. At 5 minutes post-administration, the IRdye 800 extended into the more caudal nasal cavity and within 10 minutes post-administration the dye appears at the beginning of the olfactory bulb. At 15 minutes post-administration, IRdye 800 is imaged in the rostral portion of the frontal lobe.

The trigeminal nerve and nasal cavity had high concentrations of IRdye 800 at the entry of the choana, the middle nasal concha and the maxillary sinus. High concentrations, i.e. >100 µM were seen at same locations where the trigeminal nerve passes next to the middle nasal concha, maxillary sinus and choana.

The trigeminal nerve was dissected more rostrally to the teeth and nasal cavity where the concentration was dramatically higher (about 100 µM) compared to near the brainstem (about 10 µM). Further, high concentrations of IRdye 800 were determined in the brain. Generally, ventral brain structures, those near cerebrospinal fluid (CSF), were higher in dye concentration compared to more dorsal non-CSF-contacting structures. However, IRdye 800 distributed to the entire olfactory bulb, ventral and midline portions of the anterior olfactory nucleus, the hypothalamus, medial and ventral portions of the cortex, ventral portion of the pons and entry of trigeminal roots. High concentrations of the dye concentrated in the trigeminal nuclei located on the lateral sides of the caudal brainstem and rostral cervical spinal cord.

General Experimental Discussion

Experiments 1 and 2 above demonstrate that therapeutics like lidocaine may be targeted to oral structures, facial structures and brain and spinal cord tissue/structures. The trigeminal nerve acts as a conduit to transport the therapeutic substance from the maxillary sinus cavity to the brain and spinal cord (CNS), but also in the opposite direction to other connected structures such as oral and facial structures.

Thus, the Experiments indicate that once a therapeutic substance enters the trigeminal neural/nerve pathway, it appears to travel to the trigeminal nerve's connected structures, e.g., the CNS, oral and facial structures. Consequently, the trigeminal nerve may be viewed as a bidirectional conduit that may be utilized to facilitate delivery of therapeutic substance(s) to target structure(s) and/or regions. The bidirectional characteristic of the trigeminal conduit/pathway demonstrated by the above Experiments indicate that therapeutic substances travel not only in the known rostral-to-caudal direction to the brain, but also in the caudal-to-rostral direction to oral and facial structures, e.g., the maxillary teeth.

The method of the invention administering at least one therapeutic agent to the at least one of the maxillary sinus cavities of a mammal for delivery to the CNS, oral structures and/or facial structures that are innervated by the trigeminal nerve and/or in fluid or operative communication with the maxillary sinus. Alternate embodiments may comprise administering at least one effective dose of at least one therapeutic substance to both maxillary sinuses, where the administered therapeutic substance(s) are either the same or differ from sinus to sinus. Still further alternative embodiments may comprise administering more than an initial effective dose, i.e., two or more effective doses, administered to a patient's maxillary sinus(es), so that the therapeutic substance may be delivered over time, thereby requiring a larger dose be deposited within at least one of the maxillary sinuses so that the maxillary sinus(es) serve as a therapeutic substance depot for long-term release to the target structure(s) via the trigeminal nerve conduit.

To deliver the therapeutic substance to the maxillary sinus, the therapeutic substance, either alone or in combination with other substances as a pharmaceutical composition, may be administered to the maxillary sinus, accessed via the patient's nasal cavity and the orifice of maxillary sinus. See FIG. 1 for an anatomical cutaway illustrating the nasal cavity, orifice of maxillary sinus and maxillary sinus on either side of the patient's face.

Transmission of Therapeutic Substance(s) from the Maxillary Sinus to Oral/Facial Structures As the Experiments indicate, therapeutic substances travel from the maxillary sinus along the trigeminal nerve to oral and facial structures, in a caudal-to-rostral direction. Specifically, oral and facial structures that are both innervated by the trigeminal nerve and which received a relatively high dosing of lidocaine in the Experiments as compared with intravenous administration include, without limitation: maxillary teeth, the nerve endings in the maxillary teeth, gums; the nerve endings in the gums, vasculature innervated by the trigeminal nerve, temporomandibular joint, masseter muscle, lacrimal glands, parotid glands, submandibular glands, sublingual glands, skin of the forehead, tongue, maxilla, and mandible. Conditions treated may comprise tooth pain and oral and/or facial muscle soreness as well as inflammations due to infections or other conditions.

As seen in the exemplary Experiments, one such compound may comprise lidocaine as well as structurally and functionally similar anesthetics tetracaine, articaine, marcaine, procaine, chloroprocaine, cocaine, cyclomethycaine, dimethocaine/larocaine, piperocaine, propoxycaine, procaine/novocaine, proparacaine, tetracaine/amethocaine, bupivacaine, cinchocaine/dibucaine, etidocaine, levobupivacaine, lignocaine, mepivacaine, prilocalne, ropivacaine, trimecaine and/or benzocaine for use in relieving patient anxiety over needles while achieving the desired numbing effect. Other anesthetics that may be used in various embodiments of the present invention comprise etidocaine, butamben, cocaine, dyclonine, and EMLA (lidocaine and prilocalne mixture in an oil base). Such a methodology may be used before, during and/or after a dental procedure. Other dental and/or medical/surgical procedures may make use of various embodiments of the present invention to relieve pain and discomfort, prevent and/or treat infections and/or inflammations and the like in the relevant oral and facial structures as the skilled artisan will now readily recognize. Various compounds may be used, e.g., any combination of a compound(s) selected from the group consisting of analgesic, anesthetic, anti-inflammatory compound, an antioxidant compound, and an antiviral compound.

Further, temporomandibular disorder (TMD) refers to a variety of conditions that affect temporomandibular joints, jaw muscles and facial nerves. TMD may occur when the jaw twists during opening, closing or side-motion movements. People with TMD may experience these symptoms, each of which may be treated by embodiments of the present invention: pain in or around the ear; headaches and neck ache; tenderness of the jaw or jaw muscles; jaw pain or soreness that is more prevalent in the morning or late afternoon; jaw pain when chewing, biting or yawning; difficulty opening and closing the mouth; clicking or popping noises when opening the mouth; sensitive teeth when no other dental problems can be found. Muscles involved with TMD comprise the muscles of mastication: temporalis muscle, medial pterygoid muscle and lateral pterygoid muscle. Further muscles involved with TMD, but not mastication, comprise the hylohyoid, anterio belly of the diastric and the tensor veli palatini muscles. Moreover, tiniitus (ringing of the ears) is also a symptom of TMD and a rare disorder known as tonic tensor tympani syndrome (TTTS), which may be treated by acting on the tensor tympani muscle. Each of the muscles involved with TMD listed in this paragraph are connected and/or innervated by the trigeminal nerve. Thus, the present invention may be used to treat patients with TMD. Compounds that may be used for TMD treatment comprise muscle relaxants, e.g., lorazepam and corticosteroids, e.g., hydrocortisone, which are administered in at least one effective dose to a patient's at least one maxillary sinus.

In addition, periodontal disease involving, inter alia, periodontal abscess, periodontitis and/or gingivitis may be treated with administration of at least one effective dose of an antibiotic, analgesic and/or anesthetic to a patient's at least one maxillary sinus in certain embodiments of the present invention.

Endodontic disease involving, inter alia, abscess, cellulitis, pain, pulpal infection/inflammation, periradicularly infection/inflammation may be treated by administering at least one effective dose of an antibiotic, analgesic and/or anesthetic to a patient's at least one maxillary sinus in certain embodiments of the present invention.

Orthodontic pain may also be treated with certain embodiments of the present invention by administering a long lasting anesthetic with epinephrine as well as increased bone remodeling with bone morphogenic protein (BMP) at least one effective dose to a patient's at least one maxillary sinus.

Moreover, the present invention may be used during oral surgery to treat sinus perforation and/or improve implant osseointegration with BMP.

Further, it is highly desirable to have a painless means of numbing the palatal tissue. Generally, in dental practice, the most painful injections are the nasopalatine or incisive nerve block and the greater palatine nerve block. These injections numb the anterior and posterior portions of the palate respectively. Many dentists, in fact, will not anesthetize these areas because of the extreme pain and discomfort the patient will experience as a result. Maxillary sinus delivery of the appropriate therapeutic substance, anesthetic, under various embodiments of the present invention provides a rapid and painless alternative.

Further selected uses of various embodiments of the present invention include, without limitation: 1) scaling and root planing or a "deep cleaning" done by hygienists and periodontists; 2) root canal treatment by endodontists because some palatal nerve branches will enter the periapical area and palatal nerves also innervate the tissues that the retainer clamps onto the tooth in order to maintain bacterial isolation for the tooth; 3) quadrant dentistry is an efficient, more comfortable, more rapid form of treating patients with rampant caries; 4) full mouth reconstruction requires anesthesia of quadrants of palatal tissue while the prosthodontist prepares multiple crowns near the gum line and while packing retraction cord to create an accurate impression of the crown margins; and 5) moving teeth with braces, a very painful process for adolescents or others, and this low-level chronic pain is the limiting factor for an orthodontist to move teeth. Treating with sinus delivery of long-acting anesthetic using the present invention would decrease the amount of time that patient's would have to wear braces.

Administration of certain therapeutic substance(s) to oral structures by the present invention may be beneficial in a range of situations and for a range of conditions and/or diseases. For example, before, during and/or after dental procedures involving the structures innervated by the trigeminal nerve, least one therapeutic substance from the group consisting of an analgesic, anesthetic, anti-inflammatory compound, an antioxidant compound, an antiviral compound may be delivered to the maxillary sinus in at least one effective dose or amount.

In addition, therapeutic substance(s), e.g., vaccines, antibiotics, anti-inflammatories and other drugs may be targeted via the present invention to be delivered to the nasal associated lymphatics and deep cervical nodes.

Transmission of Therapeutic Substance(s) from the Maxillary Sinus to the Brain/Central Nervous System The Experiments demonstrate that therapeutic substances travel from the maxillary sinus along the trigeminal nerve and/or other fluid or operative communication route to the patient's central nervous system. Central nervous system structures which are both innervated by the trigeminal nerve (or in fluid or operative communication with the maxillary sinus) and which received a relatively high dosing of IRdye 800 in the Experiments as compared with intravenous administration include, without limitation, the olfactory bulb, the cortex, the diencephalon, the midbrain, the cerebellum, the brainstem and upper spinal cord, the lower cervical spinal cord, the thoracic spinal cord, the lumbar spinal cord, and of course the trigeminal ganglion. Thus, the present invention may be used to treat or prevent neurologic disorder(s) as described above in patients in need thereof by administering at least one effective dose of a therapeutic substance into at least one maxillary sinus.

The optimal concentration of the active therapeutic agent will necessarily depend upon the specific neurologic agent used, the characteristics of the patient and the nature of the disease or condition for which the agent is being used. In addition, the concentration will depend upon whether the agent is being employed in a preventive or treatment capacity. Further, the stage of a particular disease or disorder, e.g., early vs. late Alzheimer's disease, may dictate the optimal concentration of the agent.

An effective amount, as herein defined, of the therapeutic agent to be administered pursuant to embodiments of the invention is the most preferred method of expression of dosage. Such effective amount is dependent upon many factors, including but not limited to, the type of disease or condition giving rise to an anticipated cerebral ischemic episode, the patient's general health, size, age, and the nature of treatment, i.e., short-term of chronic treatment. For illustrative purposes only, exemplary treatment regimens relating generally to the therapeutic agents disclosed herein, in particular deferoxamine for delivery to the patient's CNS, including dosage ranges, volumes and frequency are provided below:

Efficacious dosage range: 0.0001-1.0 mg/kg.
A more preferred dosage range may be 0.001-1.0 mg/kg.
The most preferred dosage range may be 0.05-1.0 mg/kg.
The dosage volume range may be 0.3 ml-40 ml.
The preferred dosage volume range may be 4.0 ml-15 ml.

Generally, the treatment may be given in a single dose or multiple administrations, i.e., once, twice, three or more times daily over a period of time, each administration comprising at least one effective dose, preferably one effective dose. For chronic neurologic disorders such as those diagnosed with, or at risk for, Alzheimer's disease, stroke or Parkinson's disease, the treatment may consist of at least one dose per day over an extended period of time.

Dosage ranges for embodiments of the present invention comprising anesthetics comprise:

| Compound | Efficacious Dosage Range (mg/kg) | More Preferred Dosage Range (mg/kg) | Most Preferred Dosage Range (mg/kg) |
|---|---|---|---|
| Tetracaine | 0.01-100 | 1.5-60 | 6-26 |
| Lidocaine | 0.01-897 | 1-800 | 80-300 |
| Articaine | 0.01-952 | 40-800 | 160-600 |
| Bupivacaine | 0.01-177 | 5-150 | 20-75 |
| Mepivaine | 0.01-177 | 5-150 | 20-75 |
| Prilocaine | 0.01-816 | 40-800 | 80 300 |
| Procaine | 0.01-1,749 | 1-900 | 80-600 |
| Benzocaine | 0.01-10,000 | 2-8,000 | 3-3,000 |

Alternatively, for those patients anticipating CABG surgery, the treatment may be a one-time dose to precondition the CNS in anticipation of potential cerebral ischemia. Such preconditioning may require more than one dose and may be administered from 12 hours to 1 week prior to the CABG surgery. Post-stroke treatment may require more than one dose, which may be administered several times over the course of a day, wherein this treatment regimen may encompass a week or more.

Still more alternatively, several effective doses may be administered to the maxillary sinus in embodiments of the present invention to allow for a long-term delivery over an extended time to the target organs/structures. This last embodiment essentially utilizes the maxillary sinus as a drug/therapeutic substance depository or repository, thereby reducing drastically the number of administrations (and patient compliance therewith) of the therapeutic substance(s). In the case of a vaccine, e.g., using the maxillary sinus as a vaccine depot, i.e., administering several effective doses at once may be readily be seen to produce better vaccination with a higher prolonged titer. A composition of more than one vaccine may be administered according to the present invention, which makes vaccinations easier by reducing the number of vaccination visits.

The brain concentrations that are likely to be achieved with the dosage ranges provided above are, for a single dose: 0.1 nM-50 µM. Over the course of a multi-dose treatment plan, the maximum brain concentration may be as high as 500 µM.

The formulation of the at least one therapeutic substance may comprise a water soluble or insoluble composition. The therapeutic substance may be controlled release composition as is well understood by the skilled artisan.

The delivery device may comprise of a relatively stiff catheter comprising a distal end which is curved in order to access the maxillary sinus opening and, ultimately, the maxillary sinus. A convex lens may be disposed on the distal end in operative connection with at least one fiber optic tube, preferable a plurality of fiber optic tubes in a bundle which extend operatively through the fiber optic tube to a proximal end of the fiber optic tube. The diameter of the fiber optic tube bundle is preferred to be in the range of 2 mm to 5 mm, but may also be in the range of 1 mm to 10 mm. As is known in the art, the proximal end of the fiber optic tube may then be configured to allow vision access by either the subject or a medical professional at the distal end, i.e., at the convex lens in order to facilitate navigation of the pathway through the nostril and to ultimately the maxillary sinus. In one particular embodiment, the proximal end of the catheter tube may be configured with a stiffly prebent region adapted to allow the patient to watch the insertion progress through an eyepiece attached thereto. Alternatively the proximal end may be relatively flexible so that the patient and/or health care professional may manipulate the eyepiece attached to the proximal end to enable vision access during the procedure. Still more alternatively, the procedure may be visualized on a monitor via the convex lens and fiber optic tubes which are in operative communication, either wired or wirelessly, with the monitor. Utilizing a fiber optic solution, e.g., a fiber optic bundle, makes the device very cost effective as compared with devices that require a camera and monitor as well as enabling a smaller profile/outer diameter. In addition, cost savings such as those enabled by the present invention make this delivery device/system available for use and delivery by a nurse or other healthcare professional as well as the patient or other non-healthcare professional.

The actual therapeutic substance dosage, i.e., the effective amount or at least one effective amount may be administered by different embodiments of the delivery device. A separate and smaller therapeutic substance catheter may be provided with a therapeutic substance lumen therethrough and disposed externally to, but axially translated with, the catheter tube which the patient and/or health care provider may access at the proximal end with, e.g., a syringe containing the at least one effective dose of therapeutic substance. Another method alternative may comprise the at least one effective dose to be preloaded in the distal lumen portion of the therapeutic substance lumen prior to advancement into the maxillary sinus followed by a lumen-filling bolus of saline or the like to push the at least one effective dose into the maxillary sinus. Still more alternatively the catheter tube lumen may not only comprise a plurality or bundle of fiber optic tubes, but also may comprise therapeutic substance catheter therein.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method to treat a patient's periodontal disease and the symptomatic anatomical structures innervated by the trigeminal nerve and in need thereof, comprising:
   providing a delivery device adapted for insertion into the patient's nasal cavity and operative connection with one of the patient's maxillary sinus opening;
   inserting the delivery device into the patient's nasal cavity until it reaches at least one of the patient's maxillary sinus openings;
   administering at least one effective dose of at least one therapeutic compound selected from the group consisting of an analgesic, an anesthetic, an anti-inflammatory compound, an antioxidant compound, an antiviral, an antibiotic, and bone morphogenic protein (BMP) via the delivery device through the at least one maxillary sinus opening, wherein the at least one effective dose comprises a volume of at least 0.3 milliliter;
   depositing the at least one effective dose within the maxillary sinus; and
   treating the structures innervated by the trigeminal nerve with the at least one therapeutic compound.

2. The method of claim 1, further comprising treating a patient with endodontic disease.

3. The method of claim 1, further comprising treating a patient with orthodontic pain.

4. The method of claim 1, further comprising treating a patient with temporomandibular disorder.

5. The method of claim 1, further comprising treating a patient in need of scaling, root planning and/or deep cleaning.

6. The method of claim 1, further comprising treating a patient in need of a root canal treatment.

7. The method of claim 1, further comprising treating a patient with dental caries.

8. The method of claim 1, further comprising treating a patient in need of full mouth reconstruction.

9. The method of claim 1, further comprising treating a patient before and/or while moving the patient's teeth with braces.

* * * * *